United States Patent [19]

Bjorklund et al.

[11] 4,352,566
[45] Oct. 5, 1982

[54] DETECTION OF BIREFRINGENCE IN IRREGULARLY SHAPED OBJECTS

[75] Inventors: Gary C. Bjorklund, Los Altos; David M. Bloom, Menlo Park, both of Calif.; Paul F. Liao, Fair Haven, N.J.

[73] Assignee: Bell Telephone Laboratories, Incorporated, Murray Hill, N.J.

[21] Appl. No.: 160,850

[22] Filed: Jun. 19, 1980

[51] Int. Cl.³ ............................................. G01N 21/40
[52] U.S. Cl. ..................................... 356/364; 350/3.62
[58] Field of Search ................. 356/364, 365; 350/3.6, 350/3.61, 3.62–3.64

[56] References Cited

U.S. PATENT DOCUMENTS 4,145,671  3/1979  Hellwarth ............................ 332/7.51
4,284,324  8/1981  Huignard et al. .................... 350/3.64
4,304,458  12/1981  Huignard et al. .................... 350/3.63

OTHER PUBLICATIONS

Hellwarth, R. W., "Generation of Time-Reversed Wave Fronts by Nonlinear Refraction", JOSA, vol. 67, No. 1, Jan. 77, pp. 1-3.
Yariv, A. et al., "Amplified Reflection, Phase Conjugation, and Oscillation in Degenerate Four-Wave Mixing", Optics Letters, vol. 1, No. 1, Jul. 1977, pp. 16-18.
Bloom et al., "Conjugate Wave-Front Generation and Image Reconstruction by Four-Wave Mixing", App. Phys. Letters, vol. 31, No. 9, pp. 592-594.
Martin, G. et al., "Generation of a Time-Reversed Replica of a Non-uniformly Polarized Image-Bearing Optical Beam", Optics Letters, May 1980, pp. 185-187.
Jensen et al., "Observation of the Time-Reversed Replica of a Monochromatic Optical Wave", App. Phys. Lett., vol. 32, No. 3, Feb. 1978, pp. 166-168.

Primary Examiner—John K. Corbin
Assistant Examiner—Bruce Y. Arnold
Attorney, Agent, or Firm—Michael B. Einschlag

[57] ABSTRACT

An apparatus utilizing four-wave degenerate mixing detects birefringence in irregularly shaped objects (6). Laser radiation (120) having a specified polarization is brought to a focus and then sent through the irregularly shaped object. The emerging radiation impinges upon a nonlinear material (8) to form a conjugate beam by means of four-wave degenerate mixing. The conjugate beam, which passes back through the object, is picked off and detected at a replica of the focus point. The detector (10, 11 and 12) includes a polarization detector (10) which is arranged so that a signal is detected only when the object has birefringence.

21 Claims, 2 Drawing Figures

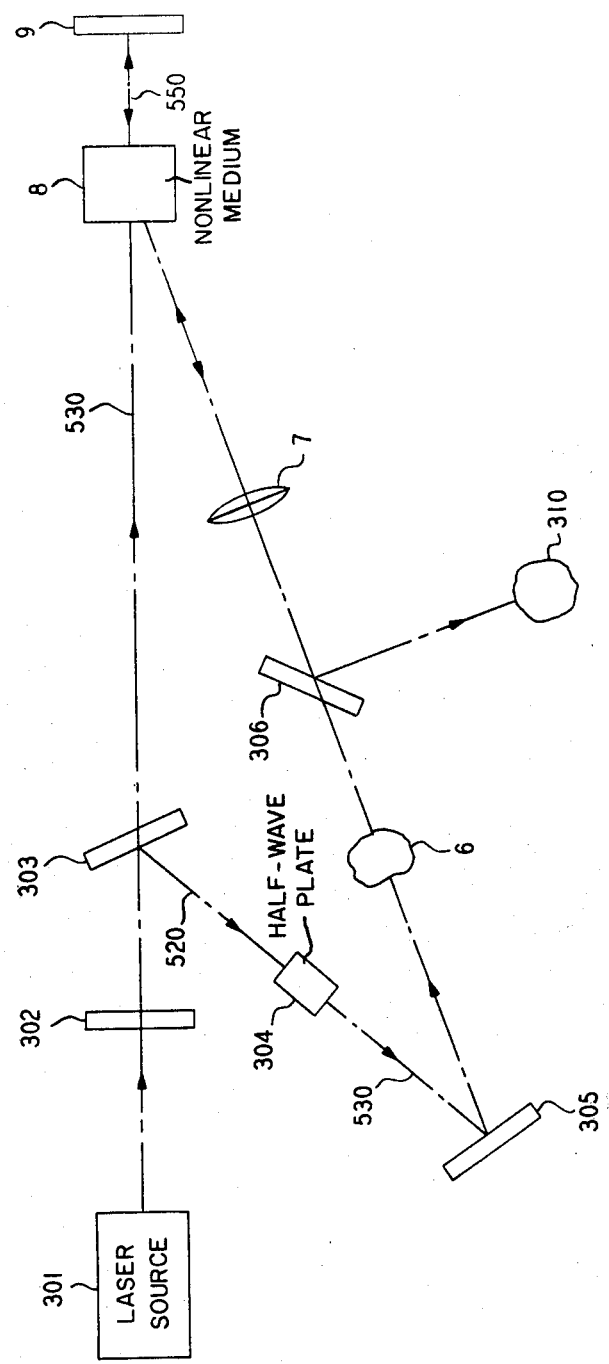

DETECTION OF BIREFRINGENCE IN IRREGULARLY SHAPED OBJECTS

BACKGROUND OF THE INVENTION

This invention pertains to the field of birefringence detection and more particularly, to the detection of birefringence using four-wave degenerate mixing.

There is great interest in producing devices which detect strain-induced birefringence in transparent irregularly shaped objects and more particularly, for apparatus that can provide this function in real time.

SUMMARY OF THE INVENTION

An apparatus for detecting birefringence in an irregularly shaped object utilizes the physical mechanism of four-wave degenerate mixing. Radiation from a laser source is brought to a focus point and then passed through the object to sample the birefringence contained therein. The emerging radiation impinges upon a material having a third-order nonlinearity in susceptibility. In a first embodiment of the present invention the material is exposed to counterpropagating laser beams at substantially the same time. This produces a beam which is conjugate to the emerging radiation. The conjugate beam passes back through the object and is detected at a position which is a replica of the original focus point. If the object has birefringence, for example birefringence induced by a strain, the polarization of the conjugate beam will be rotated from the direction of polarization of the radiation from the laser source. A polarization detector arranged to cancel radiation having the direction of polarization of the radiation from the laser source is disposed to detect the conjugate beam at the replica of the original focus point. An electrical signal is produced by the polarization detector only when the object has birefringence. Since nearly all the radiation in the conjugate beam is detected at a single focus, the detection of birefringence is independent of the shape of the object and the total electrical signal produced depends only upon the total amount of birefringence contained in the object. Only radiation which is reflected by the object does not reach the focus.

BRIEF DESCRIPTION OF THE DRAWING

A complete understanding of the present invention may be gained from a consideration of the detailed description presented hereinbelow in connection with the accompanying diagram in which:

FIG. 2 shows an embodiment of the present invention for producing an image of an irregularly shaped object which discloses only the parts having birefringence.

DETAILED DESCRIPTION

Figure 1:
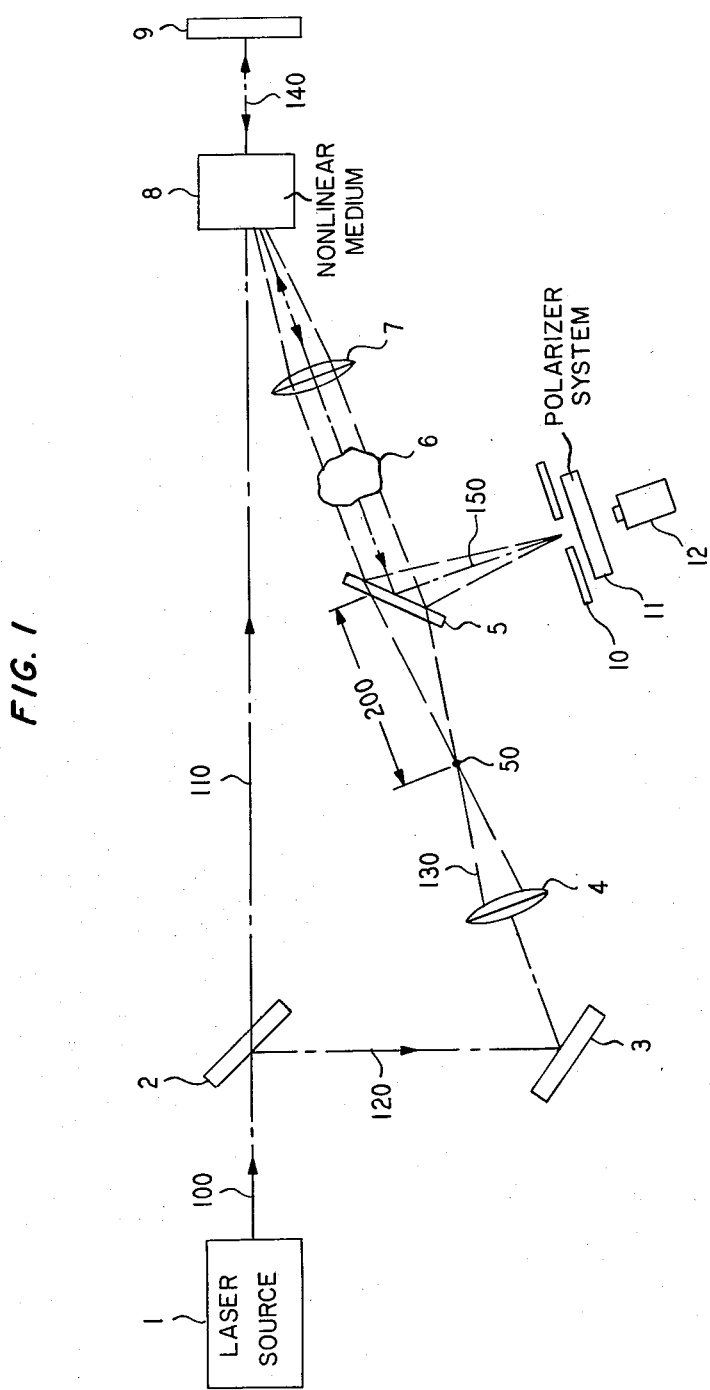
FIG. 1 shows an embodiment of the present invention for detecting birefringence in irregularly shaped objects which utilizes a single laser to produce all the required beams of laser radiation.

FIG. 1 shows a diagram of an embodiment of an apparatus constructed according to the present invention for detecting birefringence in irregularly shaped objects. Beam 100, emanating from laser source of radiation 1, impinges upon beam splitting means 2. Beam 100 is linearly polarized. Beam 120, reflected from beam splitter 2, is redirected by mirror system 3 onto focusing system 4. Focusing system 4 focuses beam 120 to a focus point 50, which focus point is depicted to be located at a distance of length 200 from a second beam splitting means 5. Beam 130 passes through beam splitting means 5 and transparent irregularly shaped object 6. Collection system 7 collects the beam that passes through object 6. The field of view of collection system 7 is made large enough to collect a substantial portion of the radiation emerging from object 6. This emerging radiation impinges upon nonlinear medium 8. Nonlinear medium 8 is made large enough so that a substantial portion of the emerging radiation collected by collecting system 7 impinges thereon.

Nonlinear medium 8 has a third-order nonlinearity in susceptibility. This nonlinearity provides four-wave mixing of the radiation incident thereon from collection system 7 and from counterpropagating pump beams. The counterpropagating pump beams are provided by beam 110, which emerges from beam splitting means 2, and beam 140, which is provided by the reflection of beam 110 from mirror system 9. As beam 110, beam 140 and the emerging radiation collected by collecting system lens 7 interact in nonlinear medium 8 by means of the physical mechanism of four-wave degenerate mixing, a fourth beam is formed. The fourth beam, a conjugate beam, is conjugate to the emerging radiation collected by collecting system 7. The conjugate beam passes back through collecting system 7 and irregularly shaped object 6. The conjugate beam is then picked off by beam splitter means 5 and directed as beam 150 to aperture 10. Aperture 10 is placed at a distance from beam splitter means 5 equal to distance 200. Beam 150 forms a replica of focus point 50 at aperture 10.

If there were no birefringence in object 6, the polarization of beam 150 at aperture 10 would be the same as the polarization of beam 100. Thus, by orienting polarizer system 11 orthogonal to the direction of linear polarization of beam 100, one can extinguish the polarization components of beam 150 which are parallel to the polarization of beam 100. However, should object 6 have some birefringence, the polarization of beam 150 will be rotated by an amount corresponding to the magnitude of the birefringence contained therein. Since polarizer system 11 is oriented to extinguish light having a polarization parallel to the polarization of beam 100, only radiation whose polarization has been rotated by the birefringence of object 6 is detected by photodetector 12. Since beam 150 is brought to a focus at aperture 10, the intensity of the radiation detected by photodetector 12 is independent of the shape of object 6 and is a measure of the total birefringence contained in object 6. Thus, the apparatus disclosed in FIG. 1 may be used to determine the presence of birefringence in an irregularly shaped object and the amount thereof. This detection and the measurement thereof is provided in real time.

Although the embodiment shown in FIG. 1 entails the use of a single laser source to provide the counterpropagating pump beams and the beam 130 which passed through irregularly shaped object 6, this is not a necessary feature in providing an apparatus constructed according to the present invention. For example, in one embodiment beams 110, 120 and 140 may be provided by 3 laser sources. In another embodiment beams 110 and 120 could be provided by a single laser source, as shown in FIG. 1, to provide a "real-time hologram" in nonlinear medium 8. This hologram may then be "read-out" by a beam from a second laser source.

In the embodiment of FIG. 1 showing the use of a single laser source, all beams impinge upon nonlinear medium 8 at substantially the same time. However, in an embodiment utilizing a second laser source of radiation to "read-out" a "real-time" hologram, the radiation from the second laser source need only impinge upon nonlinear medium 8 before the natural relaxation time of the medium. For example, the natural relaxation of a "real-time" hologram in a material such as ruby is of the order of milliseconds.

Examples of materials which may be used for nonlinear medium 8 are atomic sodium vapor, Nd:YAG, ruby, BSO and $LiNbO_3$.

We note that due to the fact that the pump beams are counterpropagating, the phasematching condition of four-wave mixing may be satisfied for any acceptance angle between the radiation impinging from collecting system 7 and the pump beams. Although the acceptance angle for the beam which passes through object 6 is not limited by phasematching when the pump beams are counterpropagating, there are phasematching conditions which restrict the amount by which the acceptance angle of the pump beams may vary and still retain the benefits of degeneracy, i.e. substantially counterpropagating pump beams. This limit is derived from the following $$|(|\vec{k}_{p1}+\vec{k}_{p2}-\vec{k}_e-(\omega/c))\times L| \lesssim \pi,$$

where $\vec{k}_{p1}$ and $\vec{k}_{p2}$ are the wave momentum vectors for the pump beams, $\vec{k}_e$ is the wave momentum vector for the emerging radiation, $\omega$ is the frequency of the radiation and L is interaction length of the three beams. If we consider the plane containing the pump beams and the emerging beam, the acceptance angle for pump beam divergence in this plane is $\sigma\theta=\lambda/L$ when the emerging and pump beams are orthogonal. The acceptance angle for pump beam divergence out of this plane is given by $\sigma\theta=(\lambda/2L)^{\frac{1}{2}}$. However, if the emerging beam is substantially aligned with the pump beams, then, the acceptance angle for divergence of the pump beams in the plane also reduces to $\sigma\theta=(\lambda/2L)^{\frac{1}{2}}$.

Thus, in general any pair of pump beams collimated to their diffraction limit to a transverse dimension in each direction such as to maintain overlap of the beams over a length L will meet these acceptance angle requirements. This is important as it will allow utilization of lower power lasers to produce the necessary power densities to drive the four-wave mixing process.

FIG. 2 shows an apparatus constructed according to a second embodiment of the present invention which provides an image of the birefringent parts of an irregularly shaped object. Laser source 301 provides beam 500 which is substantially linearly polarized. Beam 500 passes through quarter-wave plate 302 to change the polarization of beam 500 to be circularly polarized. Circularly polarized beam 510 impinges upon beam splitting means 303 to form beams 520 and 530. Beam 520 passes through half-wave plate 304 and emerges as beam 530. Beam 530 is circularly polarized, but in the opposite sense from beam 520. Beam 530 impinges upon mirror system 305 and is redirected to impinge upon irregularly shaped transparent object 6. Beam 530 emerges from object 6, passes through beam splitter 306 and is collected by collecting system 7. Collecting system 7 focuses the beam emerging from object 6 onto nonlinear medium 8 at substantially the same time that counterpropagating beams 530 and 550 impinge upon nonlinear medium 8. As described hereinabove, with regard to the embodiment shown in FIG. 1, collecting system 7 and the size of nonlinear media 8 are chosen in order to capture a substantial portion of the beam emerging from object 6. Counterpropagating beam 550 is formed when beam 530 impinges upon mirror system 9.

Due to the physical mechanism of four-wave degenerate mixing, a beam is formed which is conjugate to the beam emerging from collecting system 7. The conjugate beam propagates back through lens 7 and is picked-off by beam splitter means 306. For this embodiment of the present invention, an image, 310, is formed only if object 6 contains some birefringence. If object 6 is not birefringent, the beam emerging from object 6 will be circularly polarized in the opposite sense of the circular polarization of pump beams 530 and 550. If this is the case, then no four-wave interaction occurs in nonlinear medium 8. Thus, the apparatus of FIG. 2 obtains an image of the object 6 which shows only those portions containing birefringence. This apparatus also provides this image in real-time.

We note, as discussed hereinabove for the embodiment of FIG. 1, that this embodiment need not only use one laser source. The embodiment can be constructed using 1, 2, or 3 laser sources. We also note that an apparatus providing the same result as the apparatus of FIG. 2 can be obtained with linearly polarized pump beams of opposite polarization. The candidates for nonlinear medium 8 include the same types of materials discussed illustratively hereinabove for the apparatus shown in FIG. 1. As a further note regarding the embodiment shown in FIG. 1, we point out that the placement of a half-wave plate and a quarter-wave plate in the positions for the embodiment shown in FIG. 2 may also be used. In this instance, we would not need to have element 11 of FIG. 1 because the only radiation that would appear at aperture 10 would be due to the fact that irregularly shaped object 6 contains birefringence. This would obviate the need to use element 11 to cancel unwanted components of polarization.

We claim:

1. Apparatus for analyzing radiation that has passed through an irregularly shaped object (6), said object being transparent to radiation of at least one wavelength, said apparatus comprising:

means (1 and 2) for producing a first beam (110) and a second beam (120) having radiation which includes radiation at said one wavelength;

means (3) for directing said second beam (120) along a first predetermined path into said irregularly shaped object;

radiation collection means (7), disposed to collect radiation from said second beam which has been scattered by and through said irregularly shaped object, for directing said scattered light along a second predetermined path;

a material (8) having a third-order nonlinearity in susceptibility, disposed in said second predetermined path and in the path of said first beam;

means (9) for generating a further beam of radiation having radiation at said wavelength, which further beam counterpropagates relative to said first beam in said material, whereby a conjugate beam is generated which propagates in the opposite direction from said second predetermined path, back through said radiation collection means and said irregularly shaped object;

pick-off means (5), disposed in the path of said conjugate beam, for isolating said conjugate beam; and
means (12) for detecting radiation from said picked-off conjugate beam (150);
characterized in that:
said means for producing said first and second beams provides that said first beam and said second beam are linearly polarized;
said means for directing said second beam further comprises means (4) for bringing said second beam to a first focus point (50), said first focus point being a first distance from said pick-off means; and
said means for detecting said picked-off conjugate beam further comprises means (10 and 11), disposed to intercept radiation at a second focus point to which said picked-off conjugate beam propagates, said second focus point being at a distance from said pick-off means which is substantially equal to said first distance, for detecting the presence of a polarization which is different from said linear polarization, whereby the presence of birefringence in said irregularly shaped object is detected.

2. An apparatus in accordance with claim 1 wherein said means for generating a further beam is a source of laser radiation.

3. An apparatus for detecting birefringence in accordance with claim 2 wherein said materal having a third-order nonlinearity in susceptibility is Nd:YAG.

4. An apparatus for detecting birefringence in accordance with claim 2 wherein said material having a third-order nonlinearity in susceptibility is ruby.

5. An apparatus for detecting birefringence in accordance with claim 2 wherein said material having a third-order nonlinearity in susceptibility is BSO.

6. An apparatus for detecting birefringence in accordance with claim 2 wherein said material having a third-order nonlinearity in susceptibility is atomic sodium vapor.

7. An apparatus for detecting birefringence in accordance with claim 2 wherein said material having a third-order nonlinearity in susceptibility is LiNbO$_3$.

8. An apparatus in accordance with claim 2 wherein said means for producing said first and second beams includes a first source (1) of laser radiation for providing said first beam and a second source of laser radiation for providing said second beam.

9. An apparatus in accordance with claim 2 in which said means for producing said first and second beams comprises a first laser source (1) for providing a master beam (100) of laser radiation, said master beam having radiation at said wavelength and being linearly polarized; and
first splitting means (2), disposed to intercept said master beam, for splitting said master beam into said first beam and said second beam.

10. An apparatus in accordance with claim 1 wherein said means for generating a further beam is a mirror (9), said mirror being positioned so that its reflecting surface is normal to said first beam path after having passed through said material.

11. An apparatus for detecting birefringence in accordance with claim 1 wherein said material having a third-order nonlinearity in susceptibility is Nd:YAG.

12. An apparatus for detecting birefringence in accordance with claim 1 wherein said material having a third-order nonlinearity in susceptibility is ruby.

13. An apparatus for detecting birefringence in accordance with claim 1 wherein said material having a third-order nonlinearity in susceptibility is BSO.

14. An apparatus for detecting birefringence in accordance with claim 1 wherein said material having a third-order nonlinearity in susceptibility is atomic sodium vapor.

15. An apparatus for detecting birefringence in accordance with claim 1 wherein said material having a third-order nonlinearity in susceptibility is LiNbO$_3$.

16. An apparatus in accordance with claim 1 wherein said means for producing said first and second beams comprises a first source (1) of laser radiation for providing said first beam and a second source of laser radiation for providing said second beam.

17. An apparatus in accordance with claim 1 in which said means for producing said first and second beams comprises a first laser source (1) for providing a master beam (100) of laser radiation, said master beam having radiation at said wavelength and being linearly polarized; and
first splitting means (2), disposed to intercept said master beam, for splitting said master beam into said first beam and said second beam.

18. Apparatus for providing an image of the birefringent parts of an irregularly shaped object, said object being transparent to radiation of at least one wavelength, which comprises:
means for producing a first beam and a second beam having radiation at said wavelength and further having a first circular polarization;
polarization changing means, disposed to intercept said second beam, for changing said first circular polarization to a second circular polarization, which second circular polarization is circularly polarized in the opposite sense from said first circular polarization;
means for directing said second beam to impinge upon said irregularly shaped object;
radiation collection means, disposed to collect radiation from said second beam which has been scattered by and through said irregularly shaped object, for forming a third beam;
a material having a third-order nonlinearity in susceptibility, disposed to intercept said first beam and said third beam at substantially the same time;
means for generating a further beam of radiation at said wavelength and further having said first circular polarization, which further beam counterpropagates relative to said first beam in said material, whereby a conjugate beam is generated which propagates in the opposite direction from said third beam back through said radiation collection means; and
pick-off means, disposed to intercept said conjugate beam, for isolating said conjugate beam, whereby an image of the birefringent parts of said irregularly shaped object is formed.

19. Apparatus for detecting birefringence in an irregularly shaped object, said object being transparent to radiation of at least one wavelength, which comprises:
means for producing a first beam and a second beam having radiation at said wavelength and further having a first circular polarization;
polarization changing means, disposed to intercept said second beam, for changing said first circular polarization to a second circular polarization, which second circular polarization is circularly polarized in the opposite sense from said first circular polarization;

means, disposed to intercept said second beam, for focusing said second beam to a first focus point and directing said second beam to impinge upon said irregularly shaped object;

radiation collection means, disposed to collect radiation from said second beam which has been scattered by and through said irregularly shaped object, for forming a third beam;

a material having a third-order nonlinearity in susceptibility, disposed to intercept said first beam and said third beam at substantially the same time;

means for generating a further beam of radiation at said wavelength and further having said first circular polarization, which further beam counterpropagates relative to said first beam in said material, whereby a conjugate beam is generated which propagates in the opposite direction from said third beam back through said radiation collection means and said irregularly shaped object;

pick-off means, disposed in the path of said conjugate beam, for isolating said conjugate beam; and means for detecting said picked-off conjugate beam at a second focus point to which said picked-off conjugate beam propagates, said second focus point being at a distance from said means which is substantially equal to said first distance, whereby the presence of birefringence in said irregularly shaped object is detected.

20. An apparatus for detecting birefringence in accordance with claim 19 wherein said means for producing a first beam and a second beam includes a source of plane polarized laser radiation and a quarter-wave plate disposed to intercept said plane polarized radiation, whereby said plane polarized radiation is changed to circularly polarized radiation.

21. An apparatus for detecting birefringence in accordance with claim 20 wherein said polarization changing means is a half-wave plate.

* * * * *